(12) United States Patent
Sigurdarson et al.

(10) Patent No.: US 11,633,540 B2
(45) Date of Patent: Apr. 25, 2023

(54) SPRING STRAINING MECHANISM FOR TORSION SPRING BASED DEVICE

(71) Applicant: Novo Nordisk A/S, Bagsvaerd (DK)

(72) Inventors: Noekkvi Steinn Sigurdarson, Koebenhavn N (DK); Nicolai Michael Jensen, Koebenhaven SV (DK)

(73) Assignee: Novo Nordisk A/S, Bagsvaerd (DK)

( * ) Notice: Subject to any disclaimer, the term of this patent is extended or adjusted under 35 U.S.C. 154(b) by 53 days.

(21) Appl. No.: 16/769,068

(22) PCT Filed: Dec. 4, 2018

(86) PCT No.: PCT/EP2018/083430
§ 371 (c)(1),
(2) Date: Jun. 2, 2020

(87) PCT Pub. No.: WO2019/110559
PCT Pub. Date: Jun. 13, 2019

(65) Prior Publication Data
US 2021/0154406 A1 May 27, 2021

(30) Foreign Application Priority Data
Dec. 4, 2017 (EP) ..................... 17205131

(51) Int. Cl.
*A61M 5/20* (2006.01)
*A61M 5/32* (2006.01)

(52) U.S. Cl.
CPC ........ *A61M 5/2033* (2013.01); *A61M 5/3204* (2013.01)

(58) Field of Classification Search
CPC .............. A61M 5/2033; A61M 5/3204; A61M 5/31595; A61M 2005/202; A61M 5/3155;
(Continued)

(56) References Cited

U.S. PATENT DOCUMENTS 8,343,103 B2  1/2013  Moser
10,471,219 B2  11/2019  Jones et al.
(Continued)

FOREIGN PATENT DOCUMENTS

GB     2501897 A     11/2013
JP    2014501572 A    1/2014
(Continued)

*Primary Examiner* — Bhisma Mehta
*Assistant Examiner* — Nidah Hussain
(74) *Attorney, Agent, or Firm* — Wesley Nicolas

(57) ABSTRACT

The present invention concerns a drug delivery device (1) comprising: a housing (2) extending along a main axis, a torsion spring (5) comprising a first spring end (4) arranged stationarily with respect to the housing (2) and a second spring end (6) capable of rotation about the main axis, a rotatable shaft (80) extending along the main axis, the rotatable shaft (80) having a non-self-locking thread (81) and being axially fixed with respect to the housing (2), a spring end retainer (82) to which the second spring end (6) is attached, the spring end retainer (82) being rotationally fixed relative to the rotatable shaft (80), and a nut member (45) engaged with the non-self-locking thread (81), the nut member (45) being axially movable by translation relative to the housing (2) to thereby travel the non-self-locking thread (81) between a first position in which the torsion spring (5) is in a relaxed state and a second position in which the torsion spring (5) is in a strained state.

10 Claims, 4 Drawing Sheets

(58) Field of Classification Search
CPC .......... A61M 5/31551; A61M 5/31553; A61M 5/31583
USPC ........................................................ 604/135
See application file for complete search history.

(56)     References Cited

U.S. PATENT DOCUMENTS

| | | |
|---|---|---|
| 2013/0218128 A1 | 8/2013 | Cowe |
| 2013/0245565 A1 | 9/2013 | Leak et al. |
| 2015/0018779 A1 | 1/2015 | Nzike et al. |
| 2016/0038677 A1 | 2/2016 | Kiilerich |
| 2017/0239424 A1* | 8/2017 | Wei .................. A61M 5/31538 |

FOREIGN PATENT DOCUMENTS

| | | |
|---|---|---|
| JP | 2017535361 A | 11/2017 |
| WO | 2009092807 A1 | 7/2009 |
| WO | 2012038721 | 3/2012 |
| WO | 2016055631 | 4/2016 |

* cited by examiner

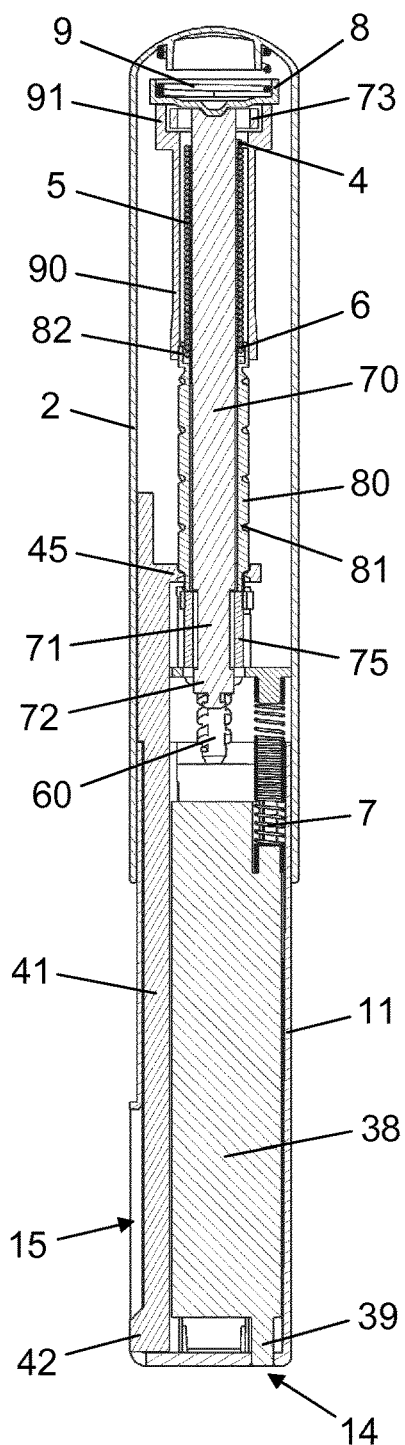
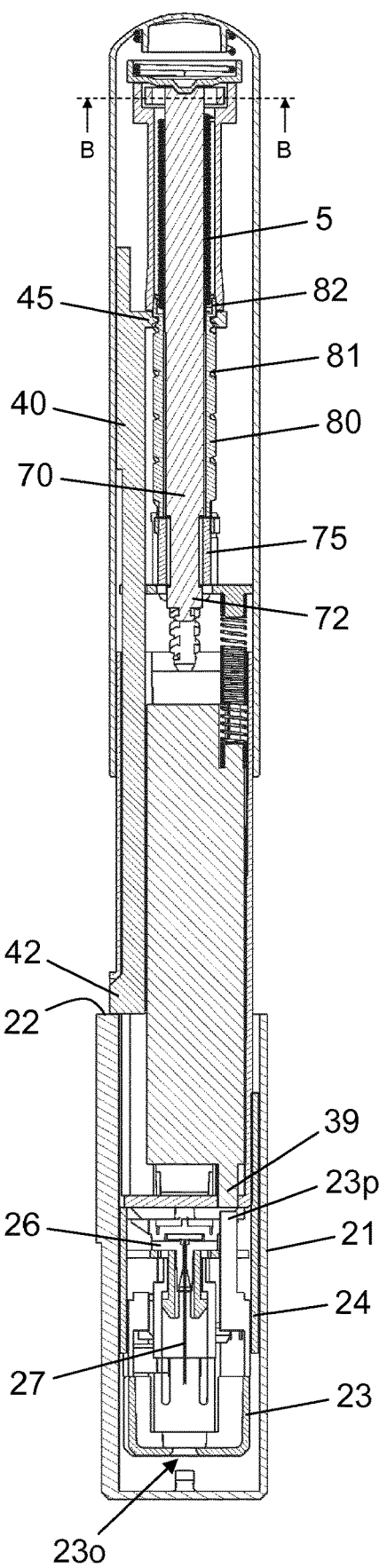
Fig. 4
Fig. 5a

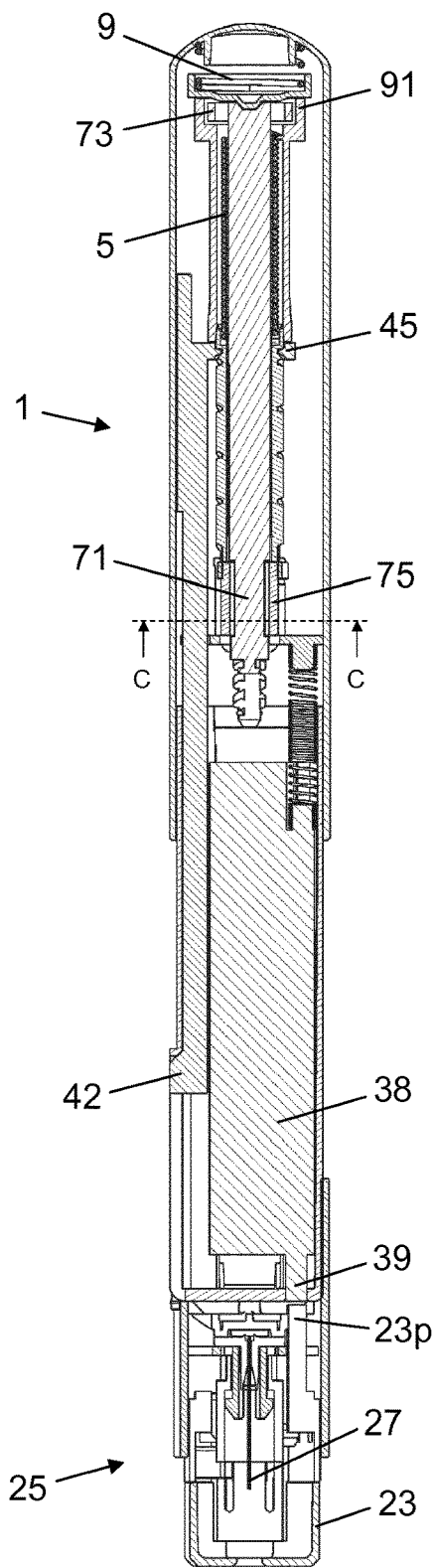
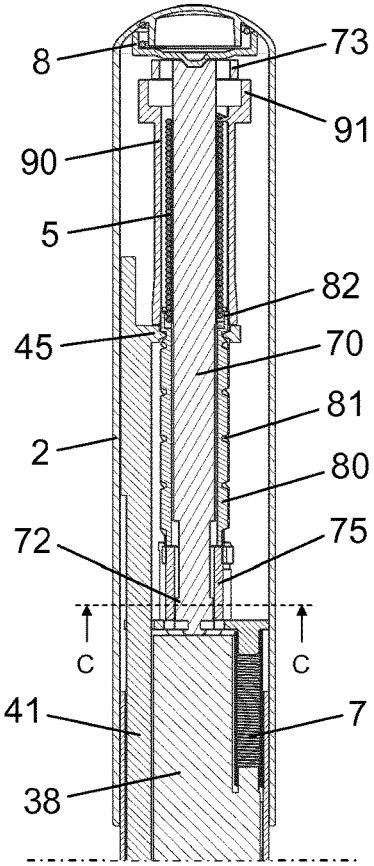
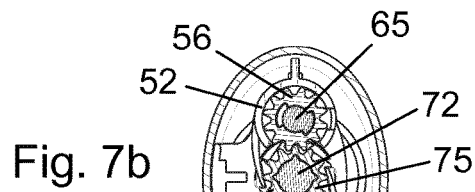
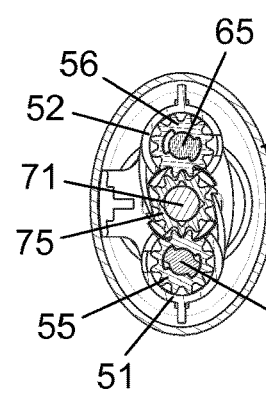
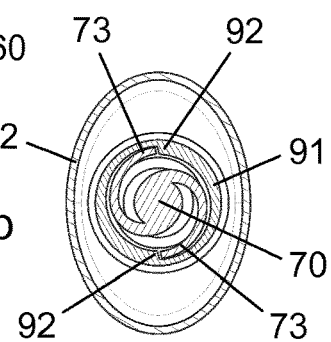
Fig. 6a
Fig. 7a
Fig. 7b
Fig. 6b
Fig. 5b

SPRING STRAINING MECHANISM FOR TORSION SPRING BASED DEVICE

CROSS-REFERENCE TO RELATED APPLICATIONS

This application is a 35 U.S.C. § 371 National Stage application of International Application PCT/EP2018/083430 (published as WO 2019/110559), filed Dec. 4, 2018, which claims priority to European Patent Application 17205131.0, filed Dec. 4, 2017; the contents of which are incorporated herein by reference.

FIELD OF THE INVENTION

The present invention relates generally to medical devices, and more specifically to automatic drug delivery devices comprising a torsion spring powered drug expelling mechanism.

BACKGROUND OF THE INVENTION

Drug delivery devices, such as injection devices, are widely used for administration of liquid drugs to people in need of therapeutic treatment. Many injection devices are capable of repeated setting and injection of either a fixed or a variable volume of drug upon operation of respective dose setting and drug expelling mechanisms in the device. Some injection devices are adapted to be loaded with a prefilled drug reservoir containing a volume of drug which is sufficient to provide for a number of injectable doses. When the reservoir is empty, the user replaces it with a new one and the injection device can thus be used again and again. Other injection devices are prefilled when delivered to the user and can only be used until the drug reservoir has been emptied, after which the device is discarded. The various injection devices comprise a drug expelling mechanism which typically expels the drug by advancing a piston in the reservoir using a motion controlled piston rod.

Some injection devices require that the user depresses a push button a certain distance towards a housing to thereby manually cause the piston rod to pressurise the reservoir and advance the piston therein for expelling of a dose. The force which must be applied to the push button to perform such an operation is often not insignificant and may cause handling problems for people with reduced finger strength and/or dexterity.

Automatic injection devices offering automatic expelling of a dose of drug in response to a release of a cocked spring are popular because the spring, once released, provides all the energy needed to complete the injection. Such devices typically only require the user to apply a small, short-duration force to trigger the injection. The spring can either be arranged to be strained before each injection, or it can be pre-strained, e.g. by the manufacturer, to store energy sufficient to occasion an emptying of the drug reservoir in one or more injections.

Such storing of energy can be challenging, however, as the majority of the injection device components are typically of plastic and thereby in risk of becoming overloaded by a heavily strained spring. In cases where the injection device has a long shelf-life and/or is used over a longer period of time this may lead to creep. The issue may be dealt with by designing the components under load in larger dimensions or by using more expensive materials but this will be contrasting the general desire to provide small and inexpensive injection devices that can be carried about discreetly.

In view hereof it is sometimes preferable to provide an automatic drug delivery device of the former type, where the majority of the spring induced load to bearing components is realised over a relatively short period of time, even though these devices require an additional user handling step in the form of a spring straining action.

In WO 2009/092807 (Novo Nordisk A/S) it is shown how the spring straining action can be incorporated as part of a handling procedure which the user normally carries out anyway. Specifically, WO 2009/092807 teaches a pen injection device, where a drive spring is axially compressed during the mounting onto, and/or dismounting from, the pen housing of a protective cap.

U.S. Pat. No. 8,343,103 (TecPharma Licensing AG) discloses a dual chamber mixing and injection device, where a discharging spring is compressed during introduction of an ampoule into the device. In this case in order to compress the spring a user is required to perform a repeated rotating action to screw an ampoule holder into the device housing. This appears cumbersome and may be viewed by some users as ergonomically challenging.

Even though WO 2009/092807 discloses use of a spring which is torsionally pre-strained the spring is essentially a compression spring, as is the one disclosed in U.S. Pat. No. 8,343,103. Neither of the two documents is concerned with solutions for easily straining a torsion spring in a drug delivery device.

SUMMARY OF THE INVENTION

It is an object of the invention to eliminate or reduce at least one drawback of the prior art, or to provide a useful alternative to prior art solutions.

In particular, it is an object of the invention to provide a torsion spring based drug delivery device where the straining of the torsion spring can be carried out easily, also by a person with reduced dexterity.

It is a further object of the invention to provide such a device where the straining of the torsion spring requires no separate handling steps for the user.

In the disclosure of the present invention, aspects and embodiments will be described which will address one or more of the above objects and/or which will address objects apparent from the following text.

A drug delivery device, such as e.g. a drug injection device, embodying the principles of the invention comprises a housing extending along a main axis, a torsion spring comprising a first spring end arranged stationarily with respect to the housing and a second spring end capable of rotation about the main axis, a rotatable shaft extending along the main axis, the rotatable shaft having a non-self-locking thread and being axially fixed with respect to the housing, a spring end retainer to which the second spring end is attached, the spring end retainer being rotationally fixed relative to the rotatable shaft, and a nut member engaged with the non-self-locking thread. The nut member is axially movable by translation relative to the housing between a first position on the non-self-locking thread in which the torsion spring is in a relaxed state and a second position on the non-self-locking thread in which the torsion spring is in a strained state.

Such a mechanism converts translational motion of the nut member to rotational motion of the rotatable shaft and the spring end retainer which thereby causes an angular displacement of the second spring end relative to the first spring end, i.e. the mechanism provides for a straining of the torsion spring based on a purely linear input.

The nut member may be coupled to a user interfacing structure which is accessible from an exterior of the housing, such as e.g. a button slidable along a housing surface, or it may itself be accessible from an exterior of the housing, allowing a user to manipulate it directly. In any case, a simple linear motion by the user will be sufficient to store energy in the torsion spring.

The drug delivery device inherently comprises a drug expelling mechanism, and the torsion spring may be adapted to power the drug expelling mechanism. Alternatively, the torsion spring may be adapted to power another mechanism in the drug delivery device.

In one aspect the invention provides a drug delivery device as defined in claim 1.

Hence, a drug delivery device is provided which comprises a housing extending along a main, or reference, axis, a drug expelling mechanism, and a torsion spring adapted to power the drug expelling mechanism. The torsion spring comprises a first spring end arranged stationarily with respect to the housing and a second spring end capable of rotation about the main axis.

The drug delivery device further comprises a rotatable shaft which extends along the main axis and is axially fixed with respect to the housing. The rotatable shaft is provided with a non-self-locking thread and carries a spring end retainer, rotationally fixed relative to the rotatable shaft, to which the second spring end is attached. Furthermore, a nut member is engaged with the non-self-locking thread. The nut member is axially movable by translation relative to the housing, i.e. the nut member is rotationally locked with respect to the housing. Thereby, due to the non-self-locking thread, the rotatable shaft rotates in response to a translational motion of the nut member, and vice versa. The nut member is thus configured to travel the non-self-locking thread between a first position in which the torsion spring is in a first energy state, e.g. a relaxed state, and a second position in which the torsion spring is in a second energy state, e.g. a strained state.

The drug delivery device further comprises an input structure for straining the torsion spring. The input structure is axially movable by translation relative to the housing and includes an interface portion which is accessible for operation, i.e. which is mechanically contactable, from an exterior of the housing, allowing for user induced translation of the input structure by interaction with the interface portion. The nut member is axially fixed with respect to the input structure, and the rotatable shaft consequently rotates in response to a translational motion of the interface portion, as the nut member travels the non-self-locking thread.

The nut member may be translated by the user immediately before initiation of a drug expelling action, whereby the nut member will travel the non-self-locking thread from the first position to the second position to strain the torsion spring, and then let go, whereby the torsion spring will release its stored energy and force the nut member to travel the non-self-locking thread from the second position back to the first position.

The nut member may be decoupled from the drug expelling mechanism during translation in a first axial direction which urges the nut member towards the second position, and operatively coupled with the drug expelling mechanism during translation in a second axial direction, i.e. opposite to the first axial direction, which urges the nut member towards the first position. Accordingly, translation of the nut member in the first axial direction has no effect on the drug expelling mechanism, whereas translation of the nut member in the second axial direction causes an activation of the drug expelling mechanism. For example, the drug expelling mechanism may comprise a piston rod configured for axial advancement, i.e. distal motion, with respect to the housing by rotation relative thereto (i.e. a helical motion), and the nut member may be rotationally decoupled from the piston rod during translation in the first axial direction and rotationally coupled with the piston rod during translation in the second axial direction.

Hence, when powering the drug expelling mechanism the torsion spring exhibits a shift between the relaxed state and the strained state as the drug delivery device is being prepared to deliver a dose of drug and as the drug delivery device expels the prepared dose. Notably, in the relaxed state the torsion spring is not completely relaxed, as it is slightly pre-strained by the manufacturer during assembly of the drug delivery device to ensure that sufficient energy is always available to deliver an entire expected dose, regardless of its size.

The drug delivery device may further comprise a releasable retaining mechanism for holding the torsion spring in the strained state. The releasable retaining mechanism may e.g. comprise a unidirectional ratchet mechanism where a ratchet arm is rotationally locked with respect to the spring end retainer and axially movable between a retained position, in which the ratchet arm is engaged with a ratchet surface that is rotationally locked with respect to the housing, and rotation of the spring end retainer in a spring unwinding direction thereby is prevented, and a released position, in which the ratchet arm is disengaged from the ratchet surface and rotation of the spring end retainer in the spring unwinding direction thereby is allowed. The ratchet arm may be biased towards the retained position, e.g. by a compression spring.

The torsion spring and the rotatable shaft may be arranged such that proximal movement of the nut member relative to the housing causes rotation of the spring end retainer in a spring straining direction. Alternatively, the torsion spring and the rotatable shaft may be arranged such that distal movement of the nut member relative to the housing causes rotation of the spring end retainer in a spring straining direction. The drug delivery device may thus be designed according to what is found most appropriate regarding the direction of translation of the nut member for straining of the torsion spring. For example, if the drug delivery device further comprises a dismountable cap for protection of a drug reservoir connected to a distal end portion of the housing the nut member may be operatively coupled with said cap and configured to undergo a spring straining distal movement relative to the housing in response to the cap being dismounted from the housing. The removal of the cap and resulting exposure of the drug reservoir, e.g. allowing for attachment thereto of an injection needle assembly, thus triggers a straining of the torsion spring and thereby an automatic readying of the drug expelling mechanism.

The input structure may comprise an axially extending rod member, and the interface portion may be arranged at an end portion of the axially extending rod member, axially spaced apart from the nut member. This will allow for operation of the nut member a certain axial distance away from its position.

In particular embodiments of the invention the nut member forms part of the input structure, thereby minimising the number of components in the device while providing a rigid and stable construction for the spring straining mechanism.

The drug delivery device may further comprise a reservoir holder for holding at least one drug reservoir. The reservoir holder may be axially fixed to a distal end portion of the housing and may comprise an axially extending track, e.g. a slot or a groove, preferably straight, or linear, in which the interface portion is slidably arranged. This allows for operation of the nut member from e.g. the distal end of the drug delivery device.

The drug delivery device may further comprise an injection needle device comprising an injection needle unit configured for attachment to a distal end portion of the reservoir holder by relative translational motion. The axially extending track may extend from the distal end portion of the reservoir holder, and a portion of the injection needle device may be configured to interact with the interface portion during attachment of the injection needle unit. Thereby, e.g. a proximal motion of the injection needle device over the reservoir holder may force the interface portion proximally in the axially extending track, and the torsion spring is thus strained automatically during attachment of the injection needle unit onto the reservoir holder.

The injection needle device may further comprise a removable needle container for housing and protecting the injection needle unit in a pre-use condition, and the portion of the injection needle device which is configured to interact with the interface portion during attachment of the injection needle unit may be or comprise a portion of the removable needle container.

The injection needle unit may comprise an injection needle member and a needle shield being axially movable relative to the injection needle member between an extended position in which a skin insertable portion of the injection needle member is covered and a retracted position in which the skin insertable portion of the injection needle member is uncovered.

In particular embodiments of the invention, e.g. the above mentioned embodiments, the injection needle member is a needle manifold comprising a needle hub, a front needle for insertion into the skin, the front needle extending distally from the needle hub, and two rear needles extending proximally from the needle hub, each rear needle being fluidly connected with the front needle and configured to establish fluid communication with a drug reservoir, and the needle shield is movable between the extended position and the retracted position to respectively cover and uncover the front needle.

In particular embodiments of the invention, e.g. the above mentioned embodiments, the unidirectional ratchet is configured to move from the retained positon to the released position in response to the needle shield moving from the extended position to the retracted position. Thereby, a drug delivery device is provided where the act of attaching an injection needle unit thereto automatically stores energy in the torsion spring, hence preparing the device for drug delivery, and where the act of inserting the skin insertable portion of the injection needle unit into the skin automatically releases the stored energy and executes the drug delivery.

It is usually recommended that injection needle units are discarded after a single use, i.a. in order to avoid skin contamination events. This recommendation is, however, sometimes ignored by users, as it involves undesired extra handling steps. A drug delivery device which offers automatic dose preparation in response to each mounting of an injection needle unit may support a handling pattern that includes taking off a used injection needle unit and replacing it with a new one. This is particularly so, if the injection needle unit is designed as a single use unit with a needle shield which locks out after the skin insertable portion of the injection needle member is pulled from the injection site.

In particular embodiments of the invention, e.g. the above mentioned embodiments, the axially extending track extends a distance which corresponds to an axial extent of the non-self-locking thread. Thereby, the interface portion may be configured to travel from end to end in the axially extending track, while the nut member travels from end to end on the non-self-locking thread, optimising the axial dimensions of the drug delivery device.

The axially extending track may be arranged in an exterior surface of the reservoir holder, whereby the movement of the interface portion will be visible to the user, which during drug expelling allows e.g. visual monitoring of the dose progression.

The spring end retainer may be a separate component being rotationally fixed with respect to the rotatable shaft, or it may alternatively form part of the rotatable shaft, in which case the number of components in the device may be reduced and a particularly stable interface to the torsion spring may be provided.

In the present context the terms "distal" and "proximal" denote positions at or directions along a drug delivery device, or a needle unit, where "distal" refers to the drug outlet end and "proximal" refers to the end opposite the drug outlet end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIG. 4 is a longitudinal section view of the drug delivery device in a pre-use state, FIG. 5*a* is a longitudinal section view of the drug delivery device following attachment of the injection needle device, and FIG. 5*b* is a cross-sectional view through section B-B thereof, FIG. 6*a* is a longitudinal section view of the drug delivery device in a ready to use state, and FIG. 6*b* is a cross-sectional view through section C-C thereof, and FIG. 7a is a longitudinal section view of a proximal portion of the drug delivery device at release of the torsion spring, and FIG. 7b is a cross-sectional view through section C-C thereof.

In the figures like structures are mainly identified by like reference numerals.

DESCRIPTION OF EXEMPLARY EMBODIMENTS

When/If relative expressions, such as "upper" and "lower", "left" and "right", "horizontal" and "vertical", "clockwise" and counter-clockwise", etc., are used in the following, these refer to the appended figures and not necessarily to an actual situation of use. The shown figures are schematic representations for which reason the configuration of the different structures as well as their relative dimensions are intended to serve illustrative purposes only.

Figure 1:
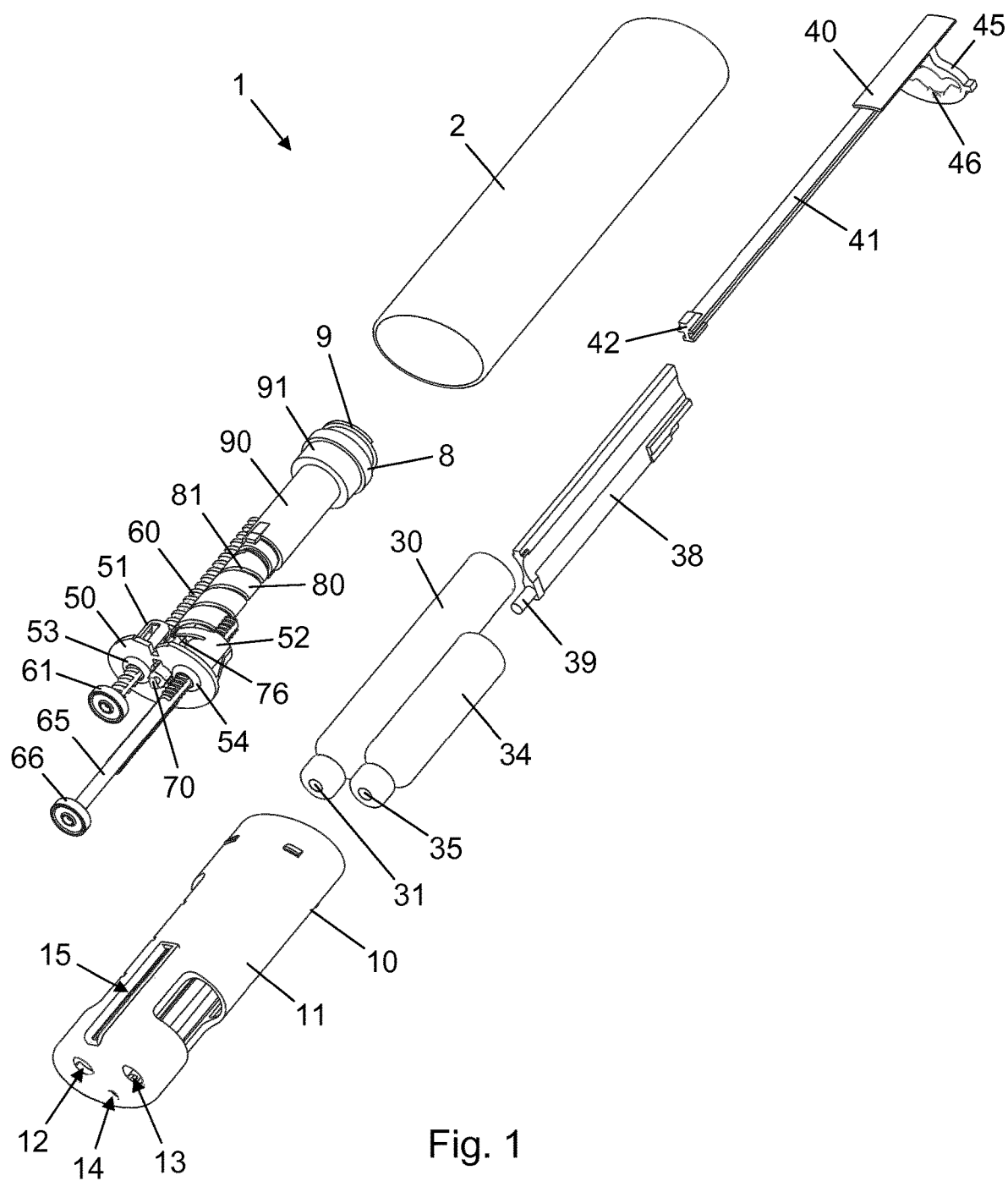
FIG. 1 is an exploded perspective view of a drug delivery device according to an exemplary embodiment of the invention.

FIG. 1 is an exploded view of a drug delivery device 1 according to an exemplary embodiment of the invention. The drug delivery device 1 is a twin chamber device in the sense that it is capable of delivering substances from two parallel reservoirs through a single needle/skin interface. The base component is an elongated housing 2 of oval cross-section, which extends along a general axis. The housing 2 accommodates a drug delivery mechanism and is fixedly connected with a reservoir holder or cartridge holder 10 having a cartridge holder body 11 accommodating a first cartridge 30, containing a first substance, and a second cartridge 34, containing a second substance, in a side-by-side arrangement.

The cartridge holder body 11 has a transversal end face with a first opening 12 providing for access to a first penetrable septum 31, which seals the first cartridge 30 distally, a second opening 13 providing for access to a second penetrable septum 35, which seals the second cartridge 34 distally, and a third opening 14 providing an interface to a trigger mechanism for the drug delivery mechanism, as will be explained below. Further, an axial slot 15 is provided in an upper side wall of the cartridge holder body 11, extending proximally from the transversal end face. The first cartridge 30 is sealed proximally by a first slidable piston (not visible) and the second cartridge 34 is sealed proximally by a second slidable piston (not visible).

The drug expelling or delivery mechanism comprises a first piston rod 60 for advancing the first slidable piston in the first cartridge 30 via a first piston washer 61, and a second piston rod 65 for advancing the second slidable piston in the second cartridge 34 via a second piston washer 66. The two piston rods 60, 65 are carried by a chassis 50 which is fixed within the housing 2. The first piston rod 60 is threadedly connected with a first nut 53 in the chassis 50, while the second piston rod 65 is threadedly connected with a second nut 54 in the chassis 50. An activation rod 70 extends through a hole in the chassis 50 between the two nuts 53, 54.

On its proximal side the chassis 50 carries a first bearing 51 for a first piston rod drive sleeve 55 (see FIG. 6B) and a second bearing 52 for a second piston rod drive sleeve 56 (see FIG. 6B). A clutch 75 (see FIG. 4) is arranged axially fixed but rotatably free between the two bearings 51, 52. The clutch 75 has an exterior toothing 76 which is permanently engaged with respective toothed exterior surfaces of the first piston rod drive sleeve 55 and the second piston rod drive sleeve 56.

A spindle or rotatable shaft 80 carrying a non-self-locking thread 81 is axially fixed with respect to the clutch 75 and with respect to a spring base 90, which is axially and rotationally locked to the housing 2. The spring base 90 houses a drive spring 5 (see FIG. 4) which is a torsion spring capable of storing and releasing rotational energy for activation of the two piston rods 60, 65. At its proximal end the spring base 90 is provided with a collar 91. The collar 91 has a proximal rim which provides an abutment interface for a cup 8 supporting a return spring 9 in the form of a compression spring.

An activator plate 38 is arranged axially slidably in the cartridge holder body 11 between the two cartridges 30, 34. The activator plate 38 comprises an axially protruding pin 39 and is biased by an activator bias spring 7 (see FIG. 4) towards a distal position in which the pin 39 is flush with the transversal end face in the third opening 14.

Extending within both the housing 2 and the cartridge holder body 11 is an input structure or loader 40 (also shown in FIG. 5a), which comprises a rod 41 terminating distally in an interface portion or rod end portion 42, and a loader nut or nut member 45. The loader nut or nut member 45 has a thread segment 46 which is engaged with the non-self-locking thread 81, and the interface portion or rod end portion 42 is arranged slidably in the axial slot 15, providing for a well-defined axial motion of the input structure or loader 40 relative to the housing 2 and the cartridge holder 10.

Figure 2:
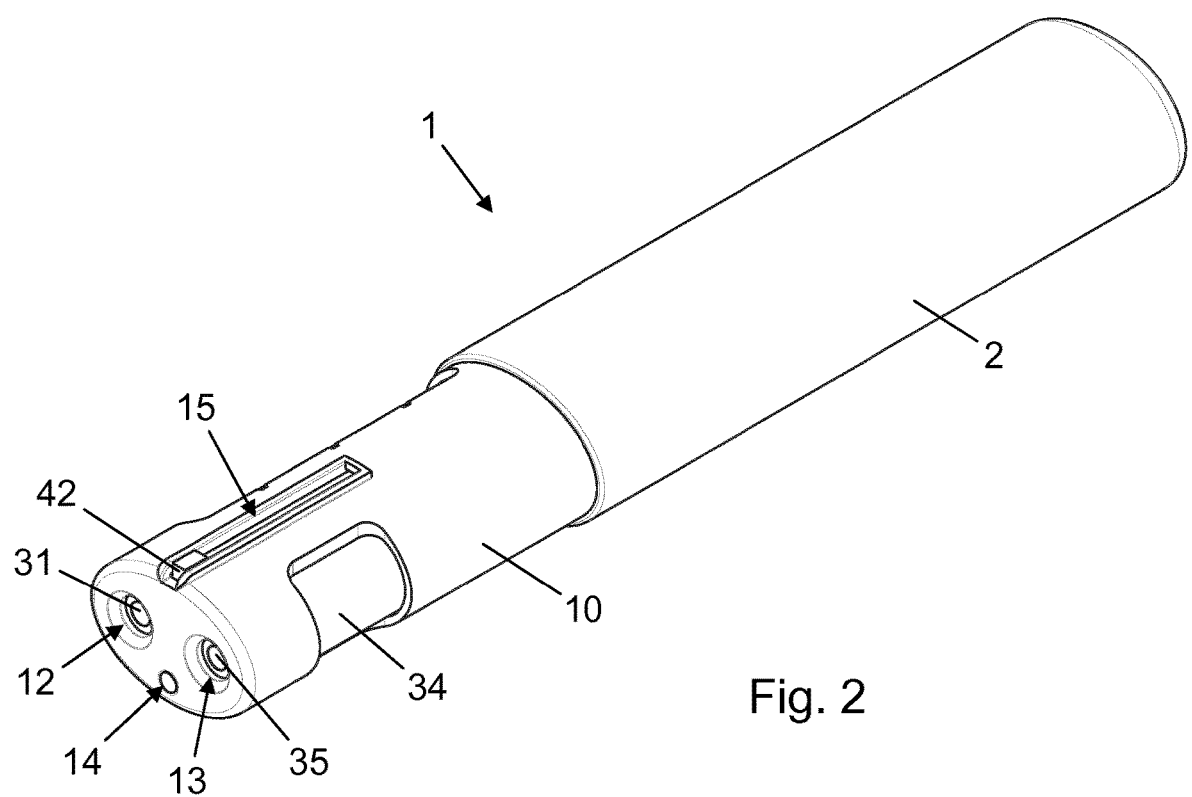
FIG. 2 is a perspective view of the drug delivery device as assembled.

FIG. 2 is a perspective view of the drug delivery device 1 in an assembled state, where the rod end portion 42 is positioned in the axial slot 15 at the transversal end face of the cartridge holder body 11.

Figure 3:
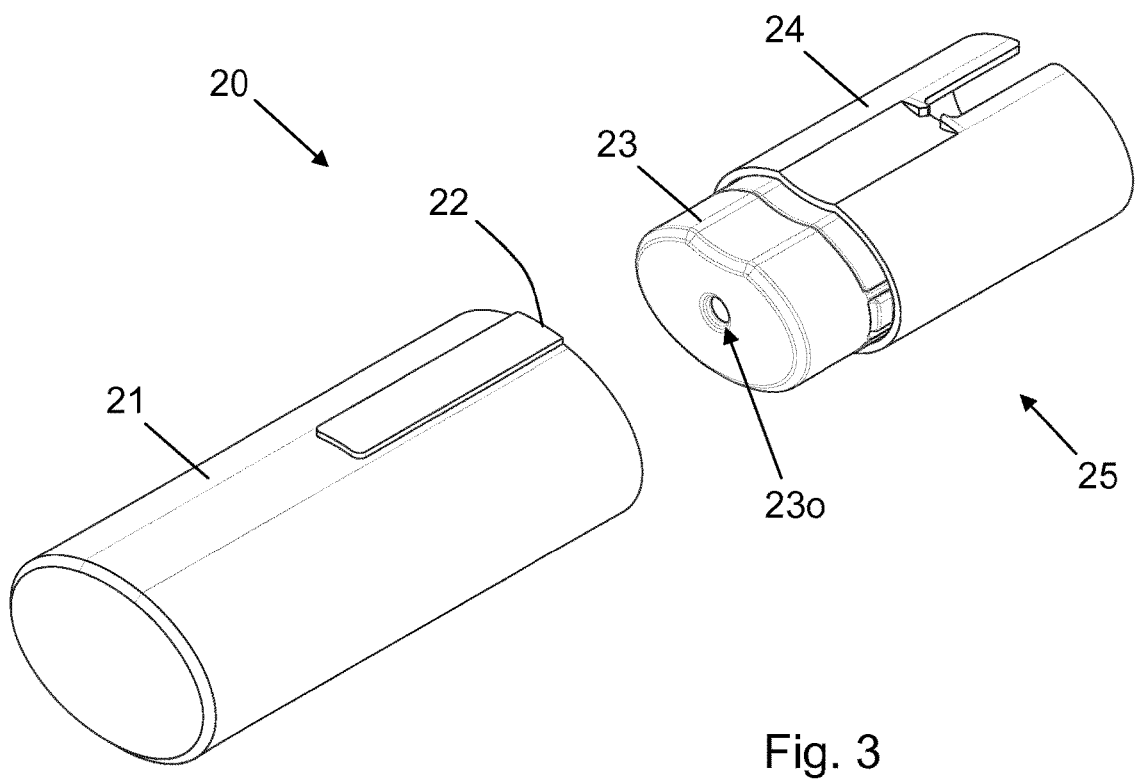
FIG. 3 is a perspective view of an injection needle device comprising a needle container and an injection needle unit for attachment to the drug delivery device.

FIG. 3 is a perspective view of a needle device 20 for use with the drug delivery device 1. The needle device 20 consists of a needle manifold 25 configured to establish fluid communication with the first cartridge 30 and the second cartridge 34 and convey the first substance and the second substance to a single outlet, and a needle container 21 for accommodating the needle manifold 25, at least in a pre-use state thereof. The needle container 21 comprises a proximal abutment surface 22 adapted to interface with the rod end portion 42 during mounting of the needle manifold 25 onto the cartridge holder body 11.

The needle manifold 25 comprises a manifold body 24 and a needle shield 23 axially displaceable relative to the manifold body 24 between an extended position and a retracted position. The needle shield 23 has a circumferentially closed side wall and a transversal end wall with a central orifice 23o.

FIG. 4 is a longitudinal section view of the drug delivery device 1 in a pre-use state before attachment of the needle manifold 25. Notably, the section is orthogonal to the plane in which the two cartridges 30, 34 are situated. The drive spring 5 has a proximal spring end 4 attached to the spring base 90 and a distal spring end 6 attached to the spring end retainer 82. The rod end portion 42 is positioned at a distal end of the axial slot 15 and the loader nut 45 is positioned at the distal end of the non-self-locking thread 81. In this pre-use state of the drug delivery device 1 the drive spring 5 is in a relaxed state in which it exhibits only a small pre-tensioning introduced by the manufacturer during the assembly process.

The activation rod 70 extends axially within the housing 2 from the collar 91 through the chassis 50. Axial splines (not visible) are provided along an exterior surface of the activation rod 70, rotationally interlocking the activation rod 70 and the spindle 80. At its proximal end the activation rod 70 has a pair of ratchet arms 73 which in the shown axial position of the activation rod 70 engages with the collar 91 and prevents clockwise rotation of the activation rod 70 relative to the spring base 90 (seen from the distal end of the drug delivery device 1). Close to its distal end the activation rod 70 is provided with a head portion 72 which borders a narrowed portion 71 arranged within the clutch 75. The head portion 72 has a toothed exterior surface which is configured for sliding reception by an interior toothing (not visible) in the clutch 75. The activation rod 70 is biased axially towards the shown distal position in the housing 2 by the return spring 9 providing a downward force to the cup 8.

FIG. 5a shows the drug delivery device 1 after attachment of the needle manifold 25 to the cartridge holder body 11. The attachment of the needle manifold 25 is achieved by mounting the needle container 21 axially over the distal portion of the cartridge holder body 11. Notably, by this action the abutment surface 22 abuts the rod end portion 42 and forces the rod 41 proximally relative to the housing 2. As a consequence the loader nut 45 is forced proximally within the housing 2, which leads the thread segment 46 to travel the non-self-locking thread 81 as the spindle 80 rotates due to the axial force application. The resulting rotation of the spring end retainer 82 causes an angular displacement of the distal spring end 6 relative to the proximal spring end 4, whereby the drive spring 5 becomes strained. When the needle manifold 25 is properly attached to the cartridge holder body 11 the rod end portion 42 is positioned at a proximal end of the axial slot 15 and the thread segment 46 is positioned at a proximal end of the non-self-locking thread 81. The drive spring 5 is now in a strained state in which it stores rotational energy releasable for activation of the two piston rods 60, 65.

The proximal displacement of the loader nut 45 which causes the spindle 80 to rotate also causes the activation rod 70 to rotate due to the splined connection between the two. However, since in the distal position of the activation rod 70 the narrowed portion 71 is positioned within the clutch 75 no rotation is transferred to the clutch 75, and the two piston rods 60, 65 are thus not activated.

The figure also shows that when the needle manifold 25 is attached to the cartridge holder body 11 a pusher 23p axially connected to the needle shield 23 is aligned with the third opening 14 and positioned just distally of the pin 39. A needle hub 26 in the manifold body 24 carries and fluidly connects two parallel rear needles (not visible in this section) with a single front needle 27 adapted for insertion into a skin portion of a user. One of the rear needles extends through the first opening 12 and the first penetrable septum 31 into an interior of the first cartridge 30, while the other rear needle extends through the second opening 13 and the second penetrable septum 35 into an interior of the second cartridge 34.

FIG. 5b is a cross-sectional view through section B-B of FIG. 5a, revealing the unidirectional ratchet interface between the activation rod 70 and the collar 91 which comprises a pair of opposite radial protrusions 92 on an interior surface portion of the collar 91 acting as stop surfaces for the pair of ratchet arms 73. In the strained state of the drive spring 5 the radial protrusions 92 prevent clockwise rotation of the activation rod 70, and thereby of the spring end retainer 82, relative to the housing 2, whereby the drive spring 5 is cocked.

FIG. 6a shows the drug delivery device 1 after removal of the needle container 21. The drug delivery device 1 is now in a ready to use state, and a user may grab the housing 2, place the needle shield 23 on the skin at a desired place and press the entire drug delivery device 1 against the skin. This will cause the needle shield 23 to displace axially relative to the manifold body 24 from the extended position to the retracted position, whereby the front needle 27 will become exposed as it protrudes through the central orifice 23o and enters the subcutaneous tissue of the user.

The axial movement of the needle shield 23 causes the pusher 23p to abut the pin 39 and urge the activator plate 38 proximally against the biasing force from the activator bias spring 7. At some point a proximal end surface of the activator plate 38 reaches the activation rod 70 and forces the activation rod 70 proximally, compressing the return spring 9. By the proximal displacement of the activation rod 70 during the last part of the movement of the needle shield 23 to the retracted position the head portion 72 with its toothed exterior surface slides into engagement with the interior toothing of the clutch 75, rotationally interlocking the activation rod 70 and the clutch 75. Furthermore, the ratchet arms 73 slide axially relative to the radial protrusions 92 and disengage from the collar 91, releasing the drive spring 5. FIG. 7a shows a proximal portion of the drug delivery device 1 in a momentary firing state when the needle shield 23 reaches the retracted position.

Since the proximal spring end 4 is attached to the spring base 90, which is fixed in the housing 2, the rotational energy released by the drive spring 5 will cause the distal spring end 6 and the spring end retainer 82 to rotate relative to the housing 2. As the spindle 80 thus undergoes a return rotation so does the activation rod 70. However, now the activation rod 70 is rotationally coupled with the clutch 75 which means that the clutch 75 rotates accordingly. The engagement between the toothed rim 76 and the respective toothed exterior surfaces of the first piston rod drive sleeve 55 and the second piston rod drive sleeve 56 resultantly causes the first piston rod drive sleeve 55 to rotate in the first bearing 51 and the second piston rod drive sleeve 56 to rotate in the second bearing 52.

FIGS. 6b and 7b, being cross-sectional views through section C-C of FIG. 6a, respectively FIG. 7a, show the difference between the two states of the drug delivery device 1, where in the ready to use state (FIG. 6b) the clutch 75 surrounds the narrowed portion 71 and in the firing state (FIG. 7b) the clutch 75 surrounds the head portion 72. Also, both figures show that the first piston rod drive sleeve 55 has an interior surface configuration which corresponds to a cross sectional profile of the first piston rod 60 and the second piston rod drive sleeve 56 has an interior surface configuration which corresponds to a cross sectional profile of the second piston rod 65. The first piston rod 60 is thereby rotationally interlocked with the first piston rod drive sleeve 55, while the second piston rod 65 is rotationally interlocked with the second piston rod drive sleeve 56.

The rotation of the clutch 75 initiated in the firing state of the drug delivery device 1 thus essentially causes a rotation of the first piston rod 60, which thereby advances helically into the first cartridge 30 due to the threaded interface with the first nut 53, as well as a rotation of the second piston rod 65, which thereby advances helically into the second cartridge 34 due to the threaded interface with the second nut 54. The respective movements of the two piston rods 60, 65 cause a dose of the first substance to be expelled from the first cartridge 30 and a dose of the second substance to be expelled from the second cartridge 34 through the respective rear needles and the front needle 27 into the user's body.

As the drive spring 5 unwinds and the spindle 80 rotates the loader nut 45 is forced axially in the distal direction, traveling the non-self-locking thread 81 back to the distal end thereof. During this return movement of the loader nut 45 the rod 41 and the rod end portion 42 are displaced correspondingly, whereby the rod end portion 42 travels the axial slot 15 back to the distal end thereof. The movement of the rod end portion 42 in the axial slot 15 during the unwinding of the drive spring 5 serves as a signal to the user that the drug expelling is progressing properly.

The invention claimed is:

1. A drug delivery device comprising:
   a housing extending along a main axis,
   a drug expelling mechanism,
   a torsion spring adapted to power the drug expelling mechanism, the torsion spring comprising a first spring end arranged stationarily with respect to the housing and a second spring end capable of rotation about the main axis,
   a rotatable shaft extending along the main axis, the rotatable shaft having a non-self-locking thread and being axially fixed with respect to the housing,
   a spring end retainer to which the second spring end is attached, the spring end retainer being rotationally fixed relative to the rotatable shaft,
   a nut member engaged with the non-self-locking thread, the nut member being axially movable by translation relative to the housing to thereby travel the non-self-locking thread between a first position in which the torsion spring is in a relaxed state and a second position in which the torsion spring is in a strained state, and
   an input structure operable to strain the torsion spring, the input structure being axially movable by translation relative to the housing and including an interface portion which is accessible for operation from an exterior of the housing, the nut member being axially fixed with respect to the input structure, whereby the rotatable shaft rotates in response to a translational motion of the interface portion.

2. The drug delivery device according to claim 1, wherein the torsion spring and the rotatable shaft are arranged such that proximal movement of the nut member relative to the housing causes rotation of the spring end retainer in a spring straining direction.

3. The drug delivery device according to claim 1, further comprising a releasable retaining mechanism for holding the torsion spring in the strained state, the releasable retaining mechanism comprising a ratchet arm being rotationally locked with respect to the spring end retainer and axially movable between a retained position, in which the ratchet arm is engaged with a ratchet surface rotationally locked with respect to the housing and rotation of the spring end retainer in a spring unwinding direction thereby is prevented, and a released position, in which the ratchet arm is disengaged from the ratchet surface and rotation of the spring end retainer in the spring unwinding direction thereby is allowed.

4. The drug delivery device according to claim 1, wherein the nut member forms part of the input structure.

5. The drug delivery device according to claim 1, further comprising a reservoir holder for holding at least one drug reservoir, the reservoir holder being axially fixed to a distal end portion of the housing and comprising an axially extending linear track in which the interface portion is slidably arranged.

6. The drug delivery device according to claim 5, further comprising an injection needle device comprising an injection needle unit configured for attachment to a distal end portion of the reservoir holder by relative translational motion, wherein the axially extending linear track extends from the distal end portion of the reservoir holder, and wherein a portion of the injection needle device is configured to interact with the interface portion during attachment of the injection needle unit.

7. The drug delivery device according to claim 6, wherein the injection needle device further comprises a removable needle container for housing and protecting the injection needle unit in a pre-use condition, and wherein the portion of the injection needle device which is configured to interact with the interface portion during attachment of the injection needle unit comprises an abutment portion of the removable needle container.

8. The drug delivery device according to claim 6, wherein the axially extending linear track extends a distance which corresponds to an axial extent of the non-self-locking thread.

9. The drug delivery device according to claim 5, wherein the axially extending linear track is arranged in an exterior surface of the reservoir holder.

10. The drug delivery device according to claim 1, wherein the spring end retainer forms part of the rotatable shaft.

* * * * *